US012599714B2

(12) United States Patent
Mora

(10) Patent No.: US 12,599,714 B2
(45) Date of Patent: Apr. 14, 2026

(54) QUICK-FILL LAVAGE SYSTEM

(71) Applicant: Maria Elena Hernandez Mora, Miami Springs, FL (US)

(72) Inventor: Maria Elena Hernandez Mora, Miami Springs, FL (US)

( * ) Notice: Subject to any disclaimer, the term of this patent is extended or adjusted under 35 U.S.C. 154(b) by 463 days.

(21) Appl. No.: 18/477,507

(22) Filed: Sep. 28, 2023

(65) Prior Publication Data

US 2025/0108157 A1     Apr. 3, 2025

(51) Int. Cl.
    *A61M 3/02*     (2006.01)
    *A61M 1/00*     (2006.01)

(52) U.S. Cl.
    CPC .......... *A61M 3/0245* (2013.01); *A61M 1/682* (2021.05); *A61M 3/0254* (2013.01); *A61M 3/0262* (2013.01); *A61M 3/0283* (2013.01); *A61M 2205/3334* (2013.01)

(58) Field of Classification Search
    CPC .... A61M 3/02; A61M 3/0245; A61M 3/0254; A61M 3/0262; A61M 3/0279; A61M 2205/3334; A61M 2205/075; A61M 1/682
    See application file for complete search history.

(56) References Cited

U.S. PATENT DOCUMENTS

| | | | | |
|---|---|---|---|---|
| 1,211,246 | A | * | 1/1917 | Schwartz ............ A61M 3/0262 604/37 |
| 1,762,430 | A | * | 6/1930 | Tokita ................. A61M 3/0262 604/212 |
| 3,452,745 | A | * | 7/1969 | Spitz ................... B05B 11/1015 601/161 |
| 4,136,696 | A | * | 1/1979 | Nehring, John R. ........................ A61M 3/0262 604/142 |
| 4,676,777 | A | * | 6/1987 | Watts .................. A61M 3/0229 604/249 |
| 2005/0084395 | A1 | * | 4/2005 | Kang .................. A61M 3/0283 417/390 |

FOREIGN PATENT DOCUMENTS

| | | | | |
|---|---|---|---|---|
| CA | | 2244050 A1 | * | 1/2000 .......... A61M 3/0287 |

* cited by examiner

*Primary Examiner* — Kyle Robert Thomas
(74) *Attorney, Agent, or Firm* — Ruben Alcoba, Esq.

(57) ABSTRACT

A quick-fill lavage system that is used in a medical environment to prevent the contamination of wounds. The quick-fill lavage system comprises of a gun shaped body that houses a refillable reservoir. A suction ball that is used to refill the reservoir. A one-way valve is used to dispense a liquid from the refillable reservoir. The one-way valve uses a suction tube system to connect the refillable reservoir to pull the liquid from the refillable reservoir. A dispensing tube system attaches to an outlet section of the one-way valve. The dispensing tube removes the liquid from the quick-fill lavage system. A trigger system is used to open the one-way valve to dispense the liquid in a control and manual manner.

4 Claims, 2 Drawing Sheets

QUICK-FILL LAVAGE SYSTEM

BACKGROUND

The present invention is directed to a disposable quick-fill lavage system that is used to remove debridement from a wound.

The invention is a hydro-cleaning system. The system uses solutions of sodium chloride, sterile water solutions, or super-oxidation solutions to irrigate open wounds.

The present invention is a one patient use manual device that allows a practitioner to load the solution that is going to be used to irrigate the wound and to dispense the solution.

The invention was developed to eliminate detritus from wounds, to remove non-viable tissue and exudate from wounds, and to remove bacteria from the wound bed.

The present invention eliminates the need of using a pressurized machine to clean wounds.

The present invention allows the practitioner to manually control the flow of the liquid that is dispensed from the invention.

The present invention is a lightweight ergonomic device that will require little training to use and that will allow the user to easily control the direction of the liquid that will be dispensed from the device.

The invention is a device that is not cost prohibitive to manufacture, therefore it is a device that lends itself to be disposable. The device is a one-time use device that is cost effective.

The present invention provides a disposable quick-fill lavage system that does not need gravity or a powered pump to dispense a solution.

SUMMARY

The present invention is a quick-fill lavage system that is used to prevent the contamination of wounds. The quick-fill lavage system comprises of a gun shaped body that houses a refillable reservoir. A suction ball that is used to refill the reservoir. A one-way valve is used to dispense a liquid from the refillable reservoir. The one-way valve uses a suction tube system to connect the refillable reservoir to pull the liquid from the refillable reservoir. A dispensing tube system attaches to an outlet section of the one-way valve. The dispensing tube removes the liquid from the quick-fill lavage system. A trigger system is used to open the one-way valve to dispense the liquid in a control and manual manner.

The present invention is used by connecting an intake tip of the device to a container containing a liquid that will be used to clean a wound. The invention is loaded with a liquid via the manual manipulation of the suction ball. The invention dispenses the liquid within the reservoir via the trigger system. The pressure used to manipulate the trigger will control the flow of the liquid that is dispensed from the invention.

The reservoir, in preferred embodiments of the present invention, will hold between one hundred to two hundred milliliters.

The present invention is a latex-free device that is lightweight and portable. The device is ergonomic and easy manipulate.

An object of the present invention is to provide a portable device that will not need a powered machine to dispense the liquid from the device.

Another object of the present invention is to provide a device that will eliminate detritus from wounds.

Yet another object of the present invention is to provide a device that will allow a user to control the flow of fluid from the device.

Yet still another object of the present invention is to provide a device that is disposable.

Yet still a further object of the present invention is to provide a device that will prevent the cross-contamination of a patient.

BRIEF DESCRIPTION OF THE DRAWINGS

These and other features, aspects, and advantages of the present invention will become better understood with regards to the following description, appended claims, and drawings where:

DESCRIPTION

Figure 1:
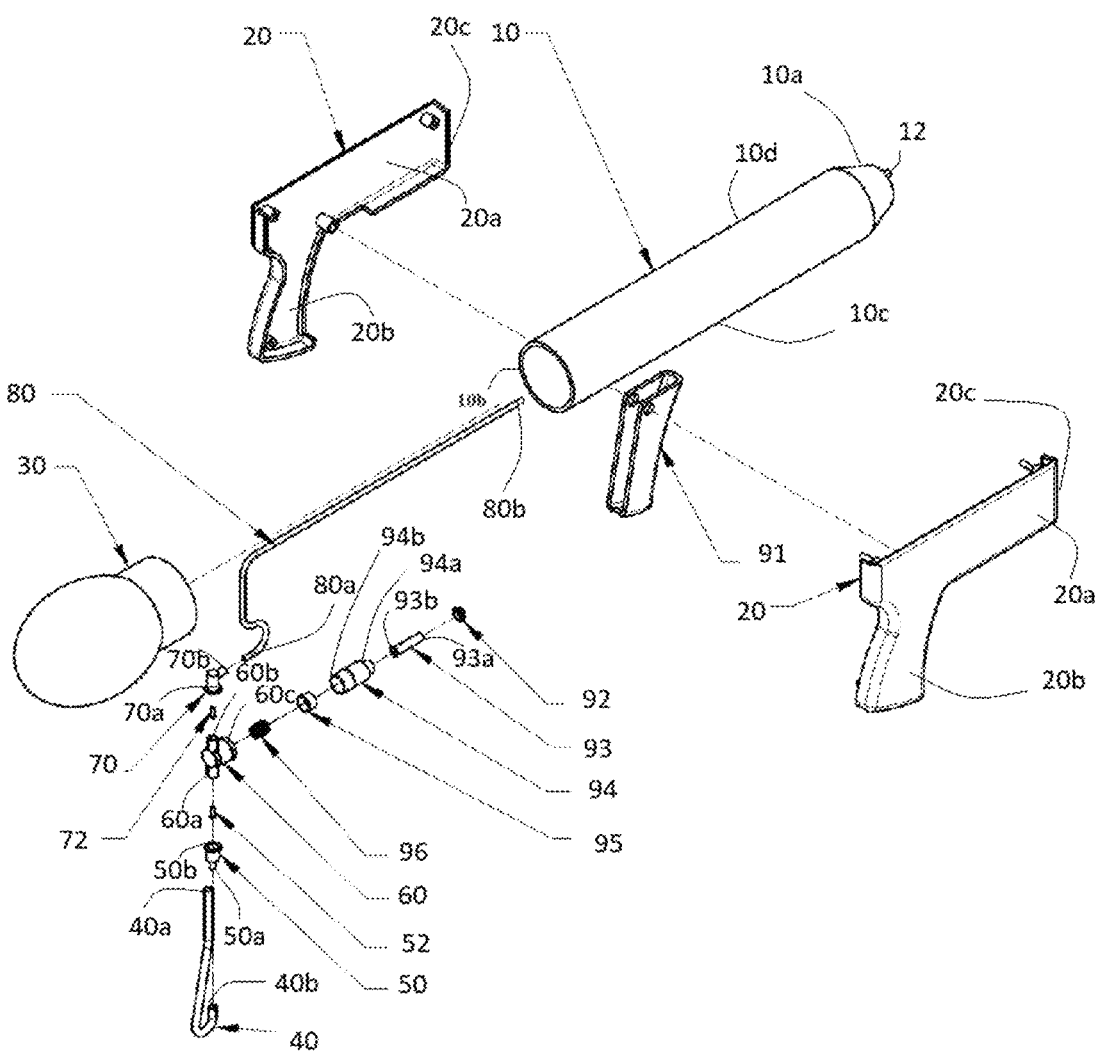
FIG. 1 shows an exploded perspective view of the present invention.
Figure 2:
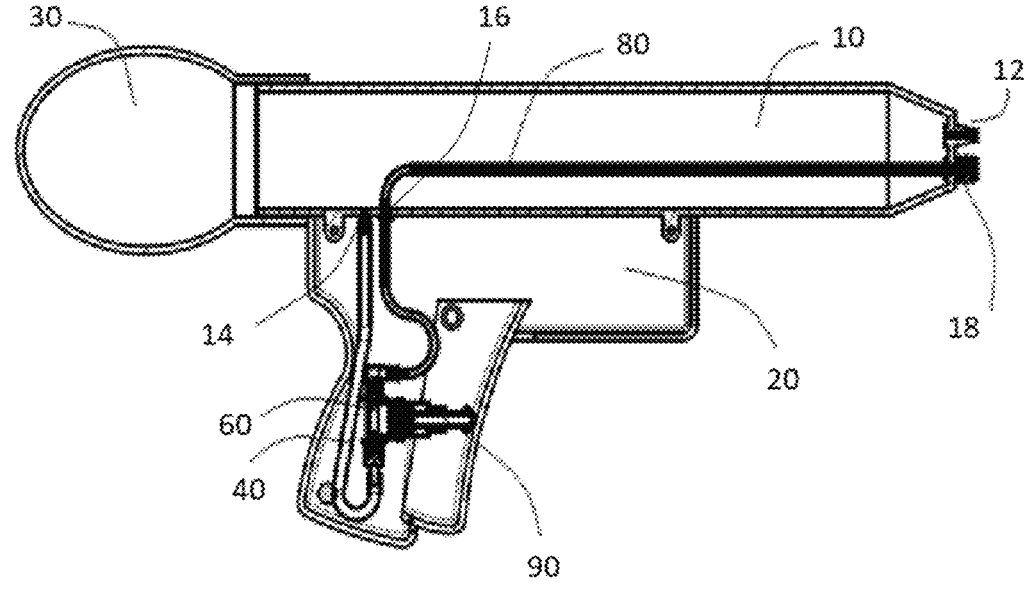
FIG. 2 shows a cross sectional view of the present invention.
Figure 3:
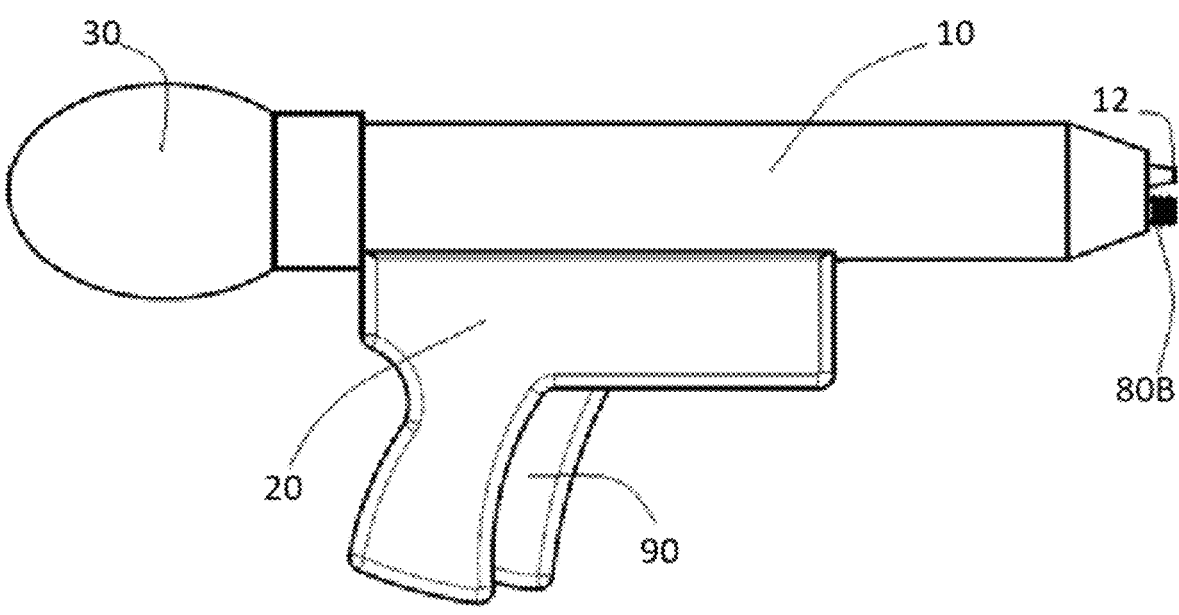
FIG. 3 shows a side view of the present invention.

As seen in FIGS. 1-3, the present invention is a quick-fill lavage system 100 that is used in a medical environment.

The quick-fill lavage system 100 comprises a reservoir 10 that has a front section 10a, a rear section 10b, a bottom section 10c, and a top section 10d, the reservoir 10 has an inlet tip 12, an outlet aperture 14, an inlet aperture 16, and a spray aperture 18, the inlet tip 12 is defined at the front section 10a of the reservoir 10, the outlet aperture 14 is defined at a rear bottom section 10c of the reservoir 10, the inlet aperture 16 is defined at a position that is adjacent to the outlet aperture 14, and the spray aperture 18 is positioned at a location that is adjacent to the inlet tip 12, the rear section 10b of the reservoir 10 is open. A gun shaped body 20 that has a barrel section 20a and a handle section 20b, the gun shaped body 20 houses the reservoir 10 so that the front section 10a of the reservoir 10 extends outward from a front section 20c of the barrel section 20a of the gun shaped body 20. A suction ball 30 that attaches to the rear section 10b of the reservoir 10. A suction tube 40 that is housed within the handle section 20b of the gun shaped body 20, the suction tube has a first end 40a and a second end 40b, the first end 40a of the suction tube 40 attaches to the outlet aperture 14 of the reservoir 10. A tube fitting 50 that has a first end 50a and a second end 50b, the first end 50a of the tube 50 fitting attaches to the second end 40b of the suction tube 40, a valve plunger 52 is housed within the tube fitting 50. A one-way valve 60 that has an inlet section 60a, an outlet section 60b, and a valve control section 60c, the one-way valve 60 is housed within the handle section 20b of the gun shaped body 20, the second end 50b of the tube fitting 50 attaches to the inlet section 60a of the one-way valve 60. A ninety-degree tube fitting 70 that houses a valve plunger 72, a first end 70a of the ninety-degree tube fitting 70 attaches to the outlet section 60b of the one-way valve 60. An ejection tube 80, a first end 80a of the ejection tube 80 attaches to a second end 70b of the ninety-degree tube fitting 70, the ejection tube 80 hermetically passes through the inlet aperture 16 of the reservoir 10, and a second end 80b of the ejection tube 80 hermetically passes through the spray aperture 18. And, a trigger system 90 that attaches to the gun shaped body 20.

In preferred embodiments, the trigger system 90 comprises of a trigger 91, a trigger cap 92 that attaches to the trigger 91, a trigger shaft 93, a first end of the trigger shaft 93a attaches to the trigger cap 92, a valve housing 94 that has a first end 94*a* a second end 94*b*, a second end 93*b* of the trigger shaft 93 inserts within the first end 94*a* of the valve housing 94, a pump cylinder 95 inserts within the second end 94*b* of the valve housing 94, and a spring 96 that is adjacent to the pump cylinder 95, the spring 96 is inserted within the second end 94*b* of the valve housing 94, the second end 94*b* of the valve housing 94 attaches to the valve control section 60*c*.

In preferred embodiments of the present invention, the reservoir 10 holds between at least 100 milliliters to at most 200 milliliters.

An advantage of the present invention is that it provides a portable device that does not need a powered machine to dispense the liquid from the device.

Another advantage of the present invention is that it provides a device that eliminates detritus from wounds.

Yet another advantage of the present invention is that it provides a device that allows a user to control the flow of fluid from the device.

Yet still another advantage of the present invention is that it provides a device that is disposable.

Yet still a further advantage of the present invention is that it provides a device that prevents the cross-contamination of a patient.

While the inventor's description contains many specificities, these should not be construed as limitations of the quick-fill lavage system, but rather as an exemplification of several preferred embodiments thereof, any other variations may be possible. Accordingly, the scope should be determined not by the embodiments illustrated, but by the specification, the drawings, and the claims and any legal equivalent thereof.

What is claimed is:

1. A quick-fill lavage system that is used in a medical environment, the quick-fill lavage system comprises:

a reservoir that has a front section, a rear section, a bottom section, and a top section, the reservoir has an inlet tip, an outlet aperture, an inlet aperture, and a spray aperture, the inlet tip is defined at the front section of the reservoir, the outlet aperture is defined at a rear bottom section of the reservoir, the inlet aperture is defined at a position that is adjacent to the outlet aperture, and the spray aperture is positioned at a location that is adjacent to the inlet tip, the rear section of the reservoir is open;

a gun shaped body that has a barrel section and a handle section, the gun shaped body houses the reservoir so that the front section of the reservoir extends outward from a front section of the barrel section of the gun shaped body;

a suction ball that attaches to the rear section of the reservoir;

a suction tube that is housed within the handle section of the gun shaped body, the suction tube has a first end and a second end, the first end of the suction tube attaches to the outlet aperture of the reservoir;

a tube fitting that has a first and a second end, the first end of the tube fitting attaches to the second end of the suction tube, a valve plunger is housed within the tube fitting;

a one-way valve that has an inlet section, an outlet section, and a valve control section, the one-way valve is housed within the handle section, the second end of the tube fitting attaches to the inlet section of the one-way valve;

a ninety-degree tube fitting that houses a valve plunger, a first end of the ninety-degree tube fitting attaches to the outlet section of the one-way valve;

an ejection tube, a first end of the ejection tube attaches to a second end of the ninety-degree tube fitting, the ejection tube hermetically passes through the inlet aperture of the reservoir, and a second end of the ejection tube hermetically passes through the spray aperture; and a trigger system that attaches to the gun shaped body.

2. The quick-fill lavage system that is used in the medical environment of claim 1, wherein the trigger system comprises of a trigger, a trigger cap that attaches to the trigger, a trigger shaft, a first end of the trigger shaft attaches to the trigger cap, a valve housing that has a first end a second end, a second end of the trigger shaft inserts within the first end of the valve housing, a pump cylinder inserts within the second end of the valve housing, and a spring that is adjacent to the cylinder and that is placed within the second end of the valve housing, the second end of the valve housing attaches to the valve control section.

3. The quick-fill lavage system that is used in the medical environment of claim 2, wherein the reservoir holds between at least 100 milliliters to at most 200 milliliters.

4. The quick-fill lavage system that is used in the medical environment of claim 1, wherein the reservoir holds between at least 100 milliliters to at most 200 milliliters.

* * * * *